(12) United States Patent
Morgan (10) Patent No.: US 9,803,196 B2
(45) Date of Patent: Oct. 31, 2017

(54) COMPOSITIONS AND METHODS FOR TREATING, DIAGNOSING AND MONITORING DISEASE

(75) Inventor: Richard Morgan, Surrey (GB)

(73) Assignee: HOX Therapeutics Limited, Ashtead, Surrey (GB)

( * ) Notice: Subject to any disclaimer, the term of this patent is extended or adjusted under 35 U.S.C. 154(b) by 0 days.

(21) Appl. No.: 14/007,932

(22) PCT Filed: Mar. 28, 2012

(86) PCT No.: PCT/GB2012/000285
§ 371 (c)(1),
(2), (4) Date: Jan. 13, 2014

(87) PCT Pub. No.: WO2012/131301
PCT Pub. Date: Oct. 4, 2012

(65) Prior Publication Data
US 2014/0154238 A1 Jun. 5, 2014

(30) Foreign Application Priority Data
Mar. 28, 2011 (GB) .................................. 1105129.9

(51) Int. Cl.
*G01N 33/574* (2006.01)
*C07K 14/47* (2006.01)
*C12N 15/113* (2010.01)
*C07K 14/705* (2006.01)
*C07K 16/18* (2006.01)

(52) U.S. Cl.
CPC ............ *C12N 15/113* (2013.01); *C07K 14/47* (2013.01); *C07K 14/705* (2013.01); *C07K 16/18* (2013.01); *C12N 15/1135* (2013.01); *C12N 15/1138* (2013.01); *G01N 33/57415* (2013.01); *G01N 33/57423* (2013.01); *G01N 33/57434* (2013.01); *G01N 33/57492* (2013.01); *C12N 2310/14* (2013.01); *G01N 2800/52* (2013.01)

(58) Field of Classification Search
CPC ....... G01N 33/57434; G01N 33/57492; G01N 2800/52; C07K 14/4748
See application file for complete search history.

(56) References Cited

U.S. PATENT DOCUMENTS

| 6,943,241 B2 * | 9/2005 | Isogai .................... C07K 14/47 |
| | | 435/252.1 |
| 7,507,549 B2 | 3/2009 | French et al. |
| 2003/0236392 A1 | 12/2003 | Isogai et al. |
| 2009/0047689 A1 | 2/2009 | Kolman et al. |
| 2010/0233187 A1 | 9/2010 | Chan et al. |

FOREIGN PATENT DOCUMENTS

| EP | 1 752 536 A1 | 2/2007 |
| WO | WO 02/078516 A2 | 10/2002 |
| WO | WO 02/086069 A2 | 10/2002 |
| WO | WO 2005/000087 A2 | 1/2005 |
| WO | WO 2010/040571 A2 | 4/2010 |

OTHER PUBLICATIONS

Giles, T.S., et al., "Gene Expression Profiling of Colonic Serrated Epithelial Lesions", United States and Canadian Academy of Pathology Annual Meeting, Feb. 28, 2011, 1 page.

Kong, W., et al., "Independent Component Analysis of Alzheimer's DNA Microarray Gene Expression Data", Molecular Neurodegeneration, 4(5): 14 pages (2009).

Notification of Transmittal of the International Search Report and the Written Opinion of the International Searching Authority for, PCT/GB2012/000285, "Compositions and Methods for Treating, Diagnosing and Monitoring Disease", date of mailing Jul. 4, 2012.

International Preliminary Report on Patentability for PCT/GB2012/000285, "Compositions and Methods for Treating, Diagnosing and Monitoring Disease", date of mailing Oct. 10, 2013.

NCBI Reference Sequence: NM_153229.2, downloaded on May 1, 2015 from http://www.ncbi.nlm.nih.gov/nuccore/NM_153229.

* cited by examiner

*Primary Examiner* — Ruixiang Li
(74) *Attorney, Agent, or Firm* — Hamilton, Brook, Smith & Reynolds, P.C.

(57) ABSTRACT

Compositions and methods which inhibit the expression of the TMEM92 gene or which inhibits the function of die TMEM92 protein can be used for treating, diagnosing and monitoring disease, for example cancer.

3 Claims, 5 Drawing Sheets

FIG. 1

```
   1 ataggtggag agaagtggga gaggtcgcag ccccgccttc tctacacagg aaagctcagt
  61 ggcccccaag ccaggatgtc ccaagcttgg gtccccggcc tcgcgcccac cttgctgttc
 121 agcctgctgg ctggccccca aaagattgca gccaaatgtg gtctcatcct tgcctgcccc
 181 aaaggattca aatgctgtgg tgacagctgc tgccaggaga acgagctctt ccctggcccc
 241 gtgaggatct tcgtcatcat cttcctggtc atcctgtccg tcttttgcat ctgtggcctg
 301 gctaagtgct tctgtcgcaa ctgcagagag ccggagccag acagcccagt ggattgccgg
 361 gggcccctgg aactgccctc catcatcccc cagagaggg tcagagtatc cctttctgcg
 421 cccccacccc cctacagtga ggtgattctg aagcccagcc tgggcccaac tcccacagag
 481 ccaccccctc cctacagctt caggcctgaa gaatataccg gggatcagag gggcattgac
 541 aacccggcct tctgagtcac ctcctgcctg gaatcttgcc atcagcaacc tcctcccag
 601 tgcctcctgg atcaagctag agactgctgg caccccagga atgtccctgc catcctgcc
 661 gtgtctctgt tcattcttgg atttaactta ttacttttc tgcttctgtt tccaccccag
 721 ctgcctctct tgtcctgagg gttaggctgg agtgacagtt tccgcccacc ccccagccca
 781 agaaagaggc tgccggaaag aaaatgctga ccattggagg tgcccaacag tagaatgggc
 841 tactgtgagg ggtagtaaga gccccatttc tggaggtatg caaatcttga ctggacagcc
 901 agctctgaga ttttatcagg gcacttctat acctgtggga cattggactg gatgagccct
 961 gagccagctt ccactcctac ctgaatagag aactcactgc acccacccac aacacatgat
1021 aaacacatgt cctcactgaa tgttactgat tgcggctgag ggcctgcctc tggctgtgtg
1081 gggaggtggg tggagaggtg agcccaggca ctgctgaggg gtgcggtgat ggggtcgctg
1141 cgccgcaatc ccaccactga tgagccacct gggaggtctg ggaggacagt ccatccatgg
1201 gccgccctcg gagagaggct tgttctagat gtattggctg tctgtttttt gatgtctctg
1261 tgtgccaaac agcctggaaa tggggtacgc gtgtcccttg tgtgggtttc ccaatccctt
1321 ccgcccaagg ctttcctggg acacatggag cccagctctc tggctgtctt accatgagaa
1381 gttggtaagt tggctgtgag ggggttggat ccaggaagca gccctgggac agcccattct
1441 gctgttgata gcaggaaacc acctgctggg agacaatggg ggtgggggaaa agcccaggag
1501 agcagtgggt ggggctgggc atccgtggag tggggcttta ggagaccttg aacggcccca
1561 ccctggaatc tcctacagga aggtgaggag gtggcaggtt ccacccttct ctaccagccc
1621 cgctcgctcg tgggagttaa ccccctaggg gagaagagtc ttcactgggg ttcgacccat
1681 gggggcctgg catagtcatg cagaatgggc cgggacaatg ccaatgcctt gggactcaga
1741 cagggctgag tgcctccacc ctgattttg cctctgcact gcgcccccac agcccactca
1801 atgccagcct ccttctccag gcagagagcc ccatgtcaat gctggccaaa gctctcagga
1861 ggattggagg tagaactggc cctggtatgc caacagggt gcctctttta gtgctctccc
1921 aataatgctc atcctggggg catcaggacg caggcaggtg gcagagctgg gggcagcttg
1981 atggcacagg cagccccaaa gatgccagga acagggactg tccgggtgtg ggttcccagt
2041 gagatagggc cctggaagga gtgcagcagt tactgacaat atagtgccag ggttggccat
2101 aggagaatga gcccaagcgt aagtggaagt ttccctttac tttcagggat tggtcagggg
2161 tggcagaaaa catgtgggtt ctttgtgtag atgtggctag ttccaattag agaagtcctg
2221 cagctgatgt tgccctcacc gtgatagcag gaggatgttg agaaatgggc ttgggagacc
2281 tggaggagaa gttaccctcg gcccagacgt tgccttcctt tcatcacagg gcctttaact
2341 cctcctaggg agtagcagag tggccctagg gaaagtggcc atcctgaaac ctagtgttgc
2401 tgtgacctgg tgacagaaat ggaaacctct gtggctcttc tggtcatcct tggtgggagt
2461 gggaatggtg tcacctttct agagggccat ctggcaccat gtaatcacgc cacagatctt
2521 tacgaagctc ctgctatgta ggaaacacta tgcctggcac tgggtatcca ttaaaatgta
2581 aaatgcacgt gacctggcaa ttccacttct agaaatgagc cttcagaagt gctcatacaa
2641 aagagctcaa taagtatcat gcactaattc attgtgccac cagagctccc tatgcagcct
2701 tttaaaagaa taaataggat ctgtagcacc aaaaaaaaaa aaaaaaa
```

FIG. 2

```
1   MSQAWVPGLA PTLLFSLLAG PQKIAAKCGL ILACPKGFKC CGDSCCQENE LFPGPVRIFV
61  IIFLVILSVF CICGLAKCFC RNCREPEPDT PVDCRGPLEL PSIIPPERVR VSLSAPPPPY
121 SEVILKPSLG PTPTEPPPPY SFRPEEYTGD QRGIDNPAF
```

COMPOSITIONS AND METHODS FOR TREATING, DIAGNOSING AND MONITORING DISEASE

RELATED APPLICATION(S)

This application is the U.S. National Stage of International Application No. PCT/GB2012/000285, filed Mar. 28, 2012, which designates the U.S., published in English, and claims priority under 35 U.S.C. §§119 or 365(c) to Great Britain Application No. 1105129.9, filed Mar. 28, 2011. The entire teachings of the above applications are incorporated herein by reference.

The present application relates to compositions and methods for treating, diagnosing and monitoring disease, for example cancer.

Cancer is one of the most prevalent diseases in the world, affecting millions of people every year. Many types of cancer are known. For the majority of cancers, effective treatments do not exist or are only effective in a small number of patients.

INCORPORATION BY REFERENCE OF MATERIAL IN ASCII TEXT FILE

This application incorporates by reference the Sequence Listing contained in the following ASCII text file:

a) File name: 47991001000SEQLIST.txt; created Sep. 26, 2013, 6 KB in size.

Accordingly, there is a need to identity new treatments for cancer and new methods of diagnosing cancer.

SUMMARY OF THE INVENTION

Figure 1:
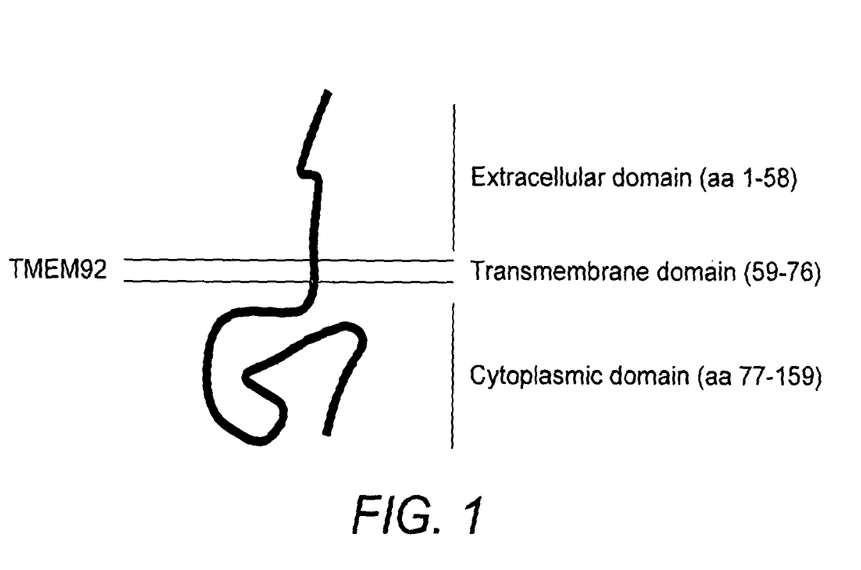
FIG. 1 shows a schematic representation of the extracellular and cytoplasmic domains of TMEM92.
Figure 3:
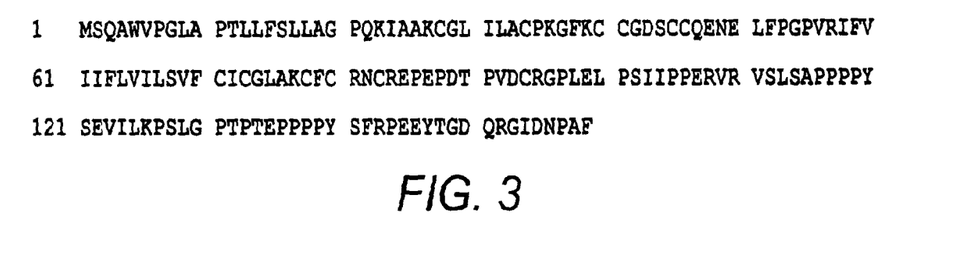
FIG. 3 shows the amino acid sequence of TMEM92 (SEQ ID NO:2)

TMEM92 (transmembrane protein 92) (NM_153229) is a previously uncharacterised gene predicted to encode a 159 amino acid (17.2 kDa) protein with a single transmembrane domain (FIG. 1).

Surprisingly, it has been found that whilst TMEM92 is not expressed in many normal adult tissues, and is expressed at only a very low level in the liver, colon, lung and uterus, it is strongly expressed in cell lines derived from prostate cancer, non-small cell lung cancer and breast cancer. As a result of the differential expression of TMEM92, its expression can be used as a biomarker, for example in relation to cancer.

Furthermore, through the use of a siRNA knock down of TMEM92 in PC3 cells (derived from a metastatic prostate cancer) and WPMY-1 cells (a non-malignant cell line derived from normal prostate fibroblasts), it has been shown herein that knock down of TMEM92 in PC3 causes a significant reduction in cell survival as compared to a control siRNA, whilst TMEM92 knock down in WPMY-1 cells does not cause cell death.

Accordingly, in one aspect of the present invention, there is provided a method for treating a disease, preferably cancer, the method comprising administering to a patient a therapeutically effective amount of a composition which inhibits the expression of the TMEM92 gene or which inhibits the function of the TMEM92 protein.

Also provided by the present invention is a composition for use in therapy, wherein the composition is capable of inhibiting the expression of the TMEM92 gene or is capable of inhibiting the function of the TMEM92 protein.

Further provided is use of a composition which inhibits the expression of the TMEM92 gene or which inhibits the function of the TMEM92 protein in therapy.

Additionally provided by the present invention is use of a composition which inhibits the expression of the TMEM92 gene or which inhibits the function of the TMEM92 protein, in the manufacture of a medicament for treating a disease, preferably cancer.

Preferably, the composition comprises a nucleic acid sequence which is (i) complementary to the nucleic acid sequence of SEQ ID NO:1 or a fragment or variant thereof; and/or (ii) hybridizable to the nucleic acid sequence of SEQ ID NO:1 or a fragment or variant thereof.

Preferably, the nucleic acid sequence is an isolated nucleic acid sequence.

Preferably, the composition comprises a nucleic acid molecule comprising a nucleic acid sequence which is (i) complementary to the nucleic acid sequence of SEQ ID NO:1 or a fragment or variant thereof; and/or (ii) hybridizable to the nucleic acid sequence of SEQ ID NO:1 or a fragment or variant thereof.

Preferably, the nucleic acid molecule comprises double stranded RNA.

Preferably, the nucleic acid molecule comprises small interfering RNA (siRNA).

As such, it is preferred that, in one embodiment of the invention, the nucleic acid sequence which is (i) complementary to the nucleic acid sequence of SEQ ID NO:1 or a fragment or variant thereof; and/or (ii) hybridizable to the nucleic acid sequence of SEQ ID NO:1 or a fragment or variant thereof, is capable of disrupting, e.g. downregulating, expression of the TMEM92 gene.

Preferably, the nucleic acid molecule further comprises vector nucleic acid sequences.

Preferably, the nucleic acid molecule further comprises nucleic acid sequences encoding a heterologous polypeptide.

Preferably, the nucleic acid molecule comprises a TMEM92-responsive promoter. As such, the nucleic acid molecule may preferably selectively drive gene expression in cells that express TMEM92. Such genes preferably include those that encode pro-drug activators or allow the replication of a lytic virus.

Preferably, the composition comprises a host cell which contains the nucleic acid molecule.

The host cell may be a mammalian host cell or a non-mammalian host cell.

Preferably, the nucleic acid sequence, which is (i) complementary to the nucleic acid sequence of SEQ ID NO:1 or a fragment or variant thereof; and/or (ii) hybridizable to the nucleic acid sequence of SEQ ID NO:1 or a fragment or variant thereof, is incorporated into a vector, for example a DNA plasmid. As such, in some embodiments of the present invention, the composition comprises a vector, for example a DNA plasmid, comprising a nucleic acid sequence which is (i) complementary to the nucleic acid sequence of SEQ ID NO:1 or a fragment or variant thereof; and/or (ii) hybridizable to the nucleic acid sequence of SEQ ID NO:1 or a fragment or variant thereof.

Preferably, the composition comprises an antibody or fragment thereof which is capable of binding to the TMEM92 protein.

Preferably, the antibody specifically binds the TMEM92 protein.

Preferably, the antibody is conjugated to a detectable marker, for example a fluorescent marker or tag. Preferably, the antibody is a monoclonal antibody. Preferably, the antibody is conjugated to a growth inhibitory agent. Preferably, the antibody is conjugated to a cytotoxic agent, for example a toxin (e.g. an immunotoxin), antibiotic, lytic enzyme or radioactive isotope.

Preferably, the composition comprises an antagonist of TMEM92 protein function, for example a small molecule antagonist.

Preferably, the composition is a pharmaceutical composition.

Preferably, the therapy is the treatment of cancer.

Preferably, the disease is cancer.

Preferably, cancer is selected from prostate cancer, non-small cell lung cancer and breast cancer.

According to another aspect of the present invention, there is provided a biomarker comprising:—

(i) a nucleic acid sequence comprising SEQ ID NO:1, or a fragment or variant thereof, or a nucleic acid molecule which comprises said nucleic acid sequence; or (ii) an amino acid sequence comprising SEQ ID NO:2, or a fragment or variant thereof, or an amino acid molecule which comprises said amino acid sequence.

In this respect, SEQ ID NO:1 corresponds to the nucleic acid sequence of the single transmembrane domain TMEM92 gene (GenBank reference number NM_153229) and SEQ ID NO:2 corresponds to the TMEM92 protein encoded thereby (NCBI accession number EAW94628, gi119615034).

Preferably, the biomarker is a cancer biomarker, for example selected from a prostate cancer biomarker, non-small cell lung cancer biomarker and breast cancer biomarker.

Preferably, the cancer is selected from prostate cancer, non-small cell lung cancer and breast cancer.

Preferably, the fragments or variants thereof comprise:—

(i) a nucleic acid sequence that has at least about 50%, or at least about 60%, or at least about 70%, or at least about 75%, or at least about 80%, or at least about 85%, or at least about 90%, or at least about 95%, or at least about 96%, or at least about 97%, or at least about 98%, or at least about 99% nucleic acid sequence identity with SEQ ID NO:1, a nucleic acid sequence that is hybridizable thereto under stringent conditions, and/or a nucleic acid sequence that is complementary thereto;

(ii) an amino acid sequence that has at least about 50%, or at least about 60%, or at least about 70%, or at least about 75%, or at least about 80%, or at least about 85%, or at least about 90%, or at least about 95%, or at least about 96%, or at least about 97%, or at least about 98%, or at least about 99% amino acid sequence identity with SEQ ID NO:2, or (iii) an amino acid sequence encoded by a nucleic acid sequence of (i).

Put another way, in accordance with part (iii) above, it is preferred that the fragments or variants thereof comprise:—

(A) an amino acid sequence encoded by a nucleic acid sequence, wherein said nucleic acid sequence has at least about 50%, or at least about 60%, or at least about 70%, or at least about 75%, or at least about 80%, or at least about 85%, or at least about 90%, or at least about 95%, or at least about 96%, or at least about 97%, or at least about 98%, or at least about 99% nucleic acid sequence identity with SEQ ID NO:1;

(B) an amino acid sequence encoded by a nucleic acid sequence, wherein said nucleic acid sequence is hybridizable under stringent conditions to a nucleic acid sequence that has at least about 50%, or at least about 60%, or at least about 70%, or at least about 75%, or at least about 80%, or at least about 85%, or at least about 90%, or at least about 95%, or at least about 96%, or at least about 97%, or at least about 98%, or at least about 99% nucleic acid sequence identity with SEQ ID NO:1; or (C) an amino acid sequence encoded by a nucleic acid sequence, wherein said nucleic acid sequence is complementary to a nucleic acid sequence that has at least about 50%, or at least about 60%, or at least about 70%, or at least about 75%, or at least about 80%, or at least about 85%, or at least about 90%, or at least about 95%, or at least about 96%, or at least about 97%, or at least about 98%, or at least about 99% nucleic acid sequence identity with SEQ ID NO:1.

Preferably, the fragments thereof comprise (i) at least four, preferably at least five, preferably at least six, preferably at least seven, preferably at least eight consecutive amino acids from SEQ ID NO:2 or (ii) a fragment of the nucleic acid sequence of SEQ ID NO:1 which encodes at least four, preferably at least five, preferably at least six, preferably at least seven, preferably at least eight consecutive amino acids from SEQ ID NO:2. Longer fragments are also preferred, for example at least about 10, 15, 20, 25, 30, 50, 75, 100, 125, and up to at least about 150 amino acids of SEQ ID NO:2 or corresponding coding fragments of SEQ ID NO: 1. Fragments may also include truncated peptides that have x amino acids deleted from the N-terminus and/or C-terminus. In such truncations, x may be 1 or more (i.e. 1, 2, 3, 4, 5, 6, 7, 8, 9, 10, 15, 20, 30, 40, 50, 60, 70, 80, 90, 100 or more), but preferably less than 125 amino acids of SEQ ID NO:2 or corresponding coding fragments of SEQ ID NO:1.

Preferably, the fragments or variants thereof are functional fragments or variants thereof.

According to another aspect of the present invention, there is provided a method for diagnosing disease, for example cancer, in a patient or for identifying a patient at risk of developing disease, for example cancer, the method comprising:

(a) determining an amount of the biomarker in a sample obtained from a patient;

(b) comparing the amount of the determined biomarker in the sample from the patient to the amount of the biomarker in a normal control;

wherein a difference in the amount of the biomarker in the sample from the patient compared to the amount of the biomarker in the normal control is associated with the presence of disease or is associated with a risk of developing disease, optionally wherein the disease is cancer, for example selected from prostate cancer, non-small cell lung cancer and breast cancer.

In preferred embodiments of the invention, the amount of the biomarker in the normal control is undetectable.

According to another aspect of the present invention, there is provided a method for diagnosing disease, for example cancer, in a patient or for identifying a patient at risk of developing disease, for example cancer, the method comprising:

determining an amount of the biomarker in a sample obtained from a patient, wherein the presence of the biomarker is associated with the presence of disease or is associated with a risk of developing disease, optionally wherein the disease is cancer, for example selected from prostate cancer, non-small cell lung cancer and breast cancer.

According to another aspect of the present invention, there is provided a method for monitoring the progression of disease, for example cancer, in a patient, the method comprising:

(a) determining an amount of the biomarker in a sample obtained from a patient;
(b) comparing the amount of the determined biomarker in the sample from the patient to the amount of the biomarker in a normal control; and
(c) repeating steps (a) and (b) at two or more time intervals,
wherein an increase in the amount of the biomarker from the patient over time is associated with an increase in the progression of disease and a decrease in the amount of the biomarker from the patient over time is associated with a decrease in the progression of disease, optionally wherein the disease is cancer, for example selected from prostate cancer, non-small cell lung cancer and breast cancer.

Accordingly, the methods of the present invention can be used to detect the onset, progression, stabilisation, amelioration and/or remission of disease.

Preferably, the control may be from the same patient from a previous sample, to thus monitor onset or progression. However, it is also preferred that the control may be normalised for a population, particularly a healthy or normal population, where there is no disease. In other words, the control may consist of the level of a biomarker found in a normal control sample from a normal subject.

Accordingly, in one example of the present invention, there is provided a method of diagnosing or monitoring the progression of disease, for example cancer, comprising detecting and/or quantifying the biomarker in a biological fluid obtained from a patient, optionally wherein the disease is cancer, for example selected from prostate cancer, non-small cell lung cancer and breast cancer.

As discussed above, it is preferred that at least two detection and/or quantification steps are provided, spaced apart temporally.

Preferably, the steps are spaced apart by a few days, weeks, years or months, to determine whether the levels of the biomarker have changed, thus indicating whether there has been a change in the progression of the disease, enabling comparisons to be made between a level of the biomarker in samples taken on two or more occasions, as an increase in the level of the biomarker over time is indicative of the onset or progression of disease, whereas a decrease in the level of the biomarker may indicate amelioration and/or remission of disease.

Preferably, the difference in the level of the biomarker is statistically significant, determined by using a "t-test" providing confidence intervals of preferably at least about 80%, preferably at least about 85%, preferably at least about 90%, preferably at least about 95%, preferably at least about 99%, preferably at least about 99.5%, preferably at least about 99.95%, preferably at least about 99.99%.

The biomarkers and methods of the invention are particularly useful in detecting early stage cancer and are more sensitive than known methods for detecting early stage cancer. Thus, the biomarkers and methods of the invention are particularly useful for confirming cancer when a patient has tested negative for cancer using conventional methods.

Prognosis and choice of treatment are dependent upon the stage of the cancer and the patient's general state of health.

Different types of prostate cancer are known. The most common starts in the prostate gland cells and is known as prostate adenocarcinoma. However, other forms of prostate cancer exist, such as, sarcomas, small cell carcinomas, and transitional cell carcinomas. The methods of the invention may be used to detect the onset of any of these types of cancer, although the detection of adenocarcinoma is preferred.

The progression of cancer is usually monitored by a staging process. This indicates how well developed the cancer is and if it has spread. The score runs from one to four, with the prognosis becoming progressively worse at each stage.

In relation to prostate cancer, the stages are as follows:—

Stage 1: Malignant cells are confined to the prostate; they have not spread to the lymph nodes or other organs; Gleason scores are between two to four, and less than five percent of the prostate is composed of tumor growth.

Stage 2: Gleason scores are five or higher, or over five percent of the gland shows abnormal growth; the cancer is still restricted to the prostate.

Stage 3: Malignant cells have spread to the seminal vesicles, but not to the lymph nodes or other organs.

Stage 4: The lymph nodes, pelvic tissue or more distant organs are affected.

In relation to non-small cell lung cancer, the stages are as follows:—

Stage 1: The cancer is localized within the lung and has not spread to any lymph nodes. Stage 1 is divided into stage 1A (tumours 3 cm or less in size), and stage 1B (tumours greater than 3 cm).

Stage 2: The cancer has spread to nearby lymph nodes, or has not spread to lymph nodes but is large, in a certain region of the main bronchus, or in a location where it invades the lung lining. Stage 2 is divided into stage 2A (a tumour 3 cm or less in size with spread to lymph nodes), or stage 2B (tumours 3 cm or greater in size with spread to lymph nodes, or present in locations such as a region of the main bronchus or invading the lung lining or chest wall).

Stage 3: The cancer has spread to tissue near the lungs. Stage 3 is divided in stage 3A (large tumours with spread to nearby lymph nodes, or any size tumour that has spread to lymph nodes further away from the tumour), and stage 3B (any size tumour that has spread to distant lymph nodes, a tumour that has invaded other structures in the chest such as the heart or esophagus, or a tumour with a malignant pleural effusion).

Stage 4: The cancer has spread to another part of the body. This can include spread to another lobe of the lung.

In relation to breast cancer, the stages are as follows:—

Stage 1: The tumour measures less than 2 cm. The lymph nodes in the armpit are not affected and there are no signs that the cancer has spread elsewhere in the body.

Stage 2: The tumour measures between 2 and 5 cm, or the lymph nodes in the armpit are affected, or both. However, there are no signs that the cancer has spread further.

Stage 3: The tumour is larger than 5 cm and may be attached to surrounding structures such as the muscle or skin. The lymph nodes are usually affected, but there are no signs that the cancer has spread beyond the breast or the lymph glands in the armpit.

Stage 4: The tumour is of any size, but the lymph nodes are usually affected and the cancer has spread to other parts of the body. This is secondary or metastatic breast cancer.

Preferably, the methods of the invention detect the onset of cancer prior to, or during stage one or stage two, more preferably stage one.

It will be appreciated that the term "early stage" as used herein can be said to refer to stage 1 and/or stage 2, as discussed above.

With regard to the term "late stage" as used herein, it will be appreciated that this term can be said to refer to stage 3 and/or stage 4.

It will be appreciated that the "early stage" and "late stage" nature of the cancer disease states can be determined by a physician. It is also envisaged that they may be associated with non-metastatic and metastatic states, respectively.

In one aspect, there are provided methods according to the present invention for detecting early stage cancer, wherein an increase between the control and the sample obtained from the patient is indicative of early stage cancer. Preferably, the increase is at least about 100%, preferably at least about 125%, preferably at least about 150%, preferably at least about 200%, preferably at least about 250%, preferably at least about 300%, preferably at least about 500%.

Also provided are methods according to the present invention for detecting late stage cancer wherein an increase between the control and the sample obtained from the patient is indicative of late stage cancer. Preferably, the increase is at least about 100%, preferably at least about 125%, preferably at least about 150%, preferably at least about 200%, preferably at least about 250%, preferably at least about 300%, preferably at least about 500%, preferably at least about 750%, preferably at least about 1000%.

Further provided are methods according to the present invention for monitoring a change in stage of cancer, wherein an increase, relative to an earlier stage sample or control is indicative of progression of the cancer from an earlier stage to later stage of disease, for example from stage 1 to stage 2, from stage 2 to stage 3, from stage 3 to stage 4, from early stage to late stage, or from stages in between, for example from stage 2A to stage 2B in accordance with cancer specific stages described above. Preferably, the increase is at least about 100%, preferably at least about 125%, preferably at least about 150%, preferably at least about 200%, preferably at least about 250%, preferably at least about 300%, preferably at least about 500%, preferably at least about 750%, preferably at least about 1000%.

It is preferred that the biomarker is indicative of the presence of disease, for example cancer or the risk of developing disease, for example cancer when present at a level of at least about 2-fold, preferably at least about 3-fold, preferably at least about 4-fold, preferably at least about 5-fold, preferably at least about 10-fold, preferably at least about 20-fold, preferably at least about 30-fold, preferably at least about 40-fold, preferably at least about 50-fold, preferably at least about 75-fold, preferably at least about 100-fold that of a normal control.

Preferably, in the methods of the present invention, it is possible to distinguish between different types of cancer by reference to (i) different levels of increase in expression of the biomarker compared to that of a normal control, and/or (ii) different levels of expression of the biomarker.

Figure 4:
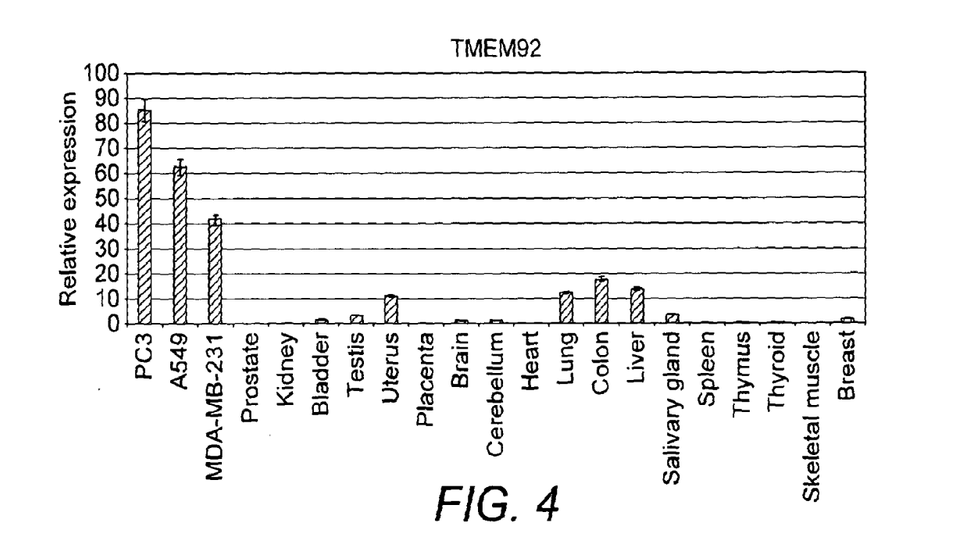
FIG. 4 shows expression of TMEM92 in the cancer derived cell lines PC3, A549 and MDA-MB-231, together with normal adult tissues. Expression is shown relative to the GAPDH gene (ratio×10,000)

For example, as shown in FIG. 4, the level of expression for PC3 (prostate cancer) was greater than that for A549 (non-small cell lung cancer) which was greater than that for MDA-MB-231 (breast cancer).

Also provided by the present invention is a method for monitoring the efficacy of a treatment for disease, for example cancer, comprising detecting and/or quantifying the presence of the biomarker in a biological sample obtained from a patient, optionally wherein the cancer is selected from prostate cancer, non-small cell lung cancer and breast cancer.

Preferably, in the methods of the present invention, detection and/or quantification of the biomarker is by one or more of MALDI-TOF, SELDI, via interaction with a ligand or ligands, 1-D or 2-D gel-based analysis systems, Liquid Chromatography, combined liquid chromatography and Mass spectrometry techniques including ICAT® or iTRAQ®, thin-layer chromatography, NMR spectroscopy, sandwich immunoassays, enzyme linked immunosorbent assays (ELISAs), radioimmunoassays (RAI), enzyme immunoassays (EIA), lateral flow/immunochromatographic strip tests, Western Blotting, immunoprecipitation, and particle-based immunoassays including using gold, silver, or latex particles, magnetic particles or Q-dots and immunohistochemistry on tissue sections.

Preferably, detection and/or quantification of the biomarker is performed on a microtitre plate, strip format, array or on a chip.

Preferably, detection and/or quantification of the biomarker is by an ELISA comprising antibodies specific for the biomarker, preferably linked to a reporter.

Preferably, detection and/or quantification of the biomarker is by a biosensor.

Preferably, the sample comprises biological fluid or tissue obtained from the patient. Preferably, the biological fluid or tissue comprises urine, cells collected from urine, circulating tumour cells, biopsy samples, semen, fluid from a lung lavage, nipple aspirate, cellular fluid, sputum, blood or saliva.

In preferred embodiments relating to prostate cancer, the sample comprises urine, semen, blood, cells collected from urine, circulating tumour cells and/or prostate biopsy samples obtained from a patient. In some embodiments, the sample comprises biological fluid or tissue obtained from the prostate of a patient.

In preferred embodiments relating to non-small cell lung cancer, the sample comprises sputum, fluid from a lung lavage, blood, circulating tumour cells and/or lung biopsy samples obtained from a patient. In some embodiments, the sample comprises biological fluid or tissue obtained from the lung of a patient.

In preferred embodiments relating to breast cancer, the sample comprises nipple aspirate (from a saline wash into nipple), blood, circulating tumour cells, and/or breast tissue biopsy samples. In some embodiments, the sample comprises biological fluid or tissue obtained from the breast of a patient.

Accordingly, it will be appreciated that, in some embodiments, the site in the body of the patient from where the sample has been obtained may correspond to a particular type of disease, for example cancer.

It is also preferred that the biological fluid is substantially or completely free of whole/intact cells. Preferably the biological fluid is free of platelets and cell debris (such as that produced upon the lysis of cells). Preferably the biological fluid is free of both prokaryotic and eukaryotic cells.

Such samples can be obtained by any number of means known in the art, such as will be apparent to the skilled person. For instance, urine samples are easily attainable, whilst blood or serum samples can be obtained parenterally by using a needle and syringe, for instance. Cell free or substantially cell free samples can be obtained by subjecting the sample to various techniques known to those of skill in the art which include, but are not limited to, centrifugation and filtration.

Although it is generally preferred that no invasive techniques are used to obtain the sample, it still may be preferable to obtain samples such as tissue homogenates, tissue sections and biopsy specimens.

Another aspect of the present invention relates to a method for treating a patient with a disease, preferably cancer, the method comprising administering to a patient a therapeutically effective amount of a biomarker of the present invention, optionally, wherein the cancer is selected from prostate cancer, non-small cell lung cancer and breast cancer.

Another aspect of the present invention relates to a method for imaging disease, for example cancer in a patient, the method comprising administering to a patient an antibody or fragment thereof that binds to a biomarker of the present invention, optionally wherein the cancer is selected from prostate cancer, non-small cell lung cancer and breast cancer.

Preferably, the antibody is conjugated to a detectable marker, for example a fluorescent marker or tag. Preferably, the antibody is a monoclonal antibody. Preferably, the antibody is conjugated to a growth inhibitory agent. Preferably, the antibody is conjugated to a cytotoxic agent, for example a toxin (e.g. an immunotoxin), antibiotic, lytic enzyme or radioactive isotope.

Reference herein to the composition is also intended to relate to the composition per se. Accordingly, another aspect of the present invention relates to a composition comprising
(A) a biomarker of the present invention;
(B) a nucleic acid sequence which is (i) complementary to the nucleic acid sequence of SEQ ID NO:1 or a fragment or variant thereof; and/or (ii) hybridizable to the nucleic acid sequence of SEQ ID NO:1 or a fragment or variant thereof;
(C) a nucleic acid molecule comprising a nucleic acid sequence which is (i) complementary to the nucleic acid sequence of SEQ ID NO:1 or a fragment or variant thereof; and/or (ii) hybridizable to the nucleic acid sequence of SEQ ID NO:1 or a fragment or variant thereof;
(D) a host cell which contains the nucleic acid molecule;
(E) a vector, for example a DNA plasmid, comprising a nucleic acid sequence which is (i) complementary to the nucleic acid sequence of SEQ ID NO:1 or a fragment or variant thereof; and/or (ii) hybridizable to the nucleic acid sequence of SEQ ID NO:1 or a fragment or variant thereof;
(F) an antibody or fragment thereof which is capable of binding to the TMEM92 protein;
(G) an antibody or fragment thereof which is capable of binding to a biomarker of the present invention; and/or
(H) an antagonist of TMEM92 protein function, for example a small molecule antagonist.

Preferably, the composition is a pharmaceutical composition.

Also provided by the present invention is a vaccine comprising a composition of the present invention, for example a biomarker of the present invention or an antibody or fragment thereof that binds to a biomarker of the present invention.

In this respect, TMEM92 is present on the outside of the cell membrane and is therefore an ideal target in relation to a vaccine.

Preferably the vaccine is a cancer vaccine, for example selected from a prostate cancer vaccine, a non-small cell lung cancer vaccine and a breast cancer vaccine.

Another aspect of the present invention relates to use of the biomarker, detectable in a body fluid, as a biomarker for disease, for example cancer, optionally wherein the cancer is selected from prostate cancer, non-small cell lung cancer and breast cancer.

Preferably, said use is in a method selected from the group consisting of: clinical screening, methods of prognosis assessment, monitoring the results of therapy, method to identify patients most likely to respond to a particular therapeutic treatment, and drug screening and development.

Another aspect of the present invention relates to use of a composition or biomarker of the present invention in the manufacture of a medicament for the treatment of disease, for example cancer, optionally wherein the cancer is selected from prostate cancer, non-small cell lung cancer and breast cancer.

Also provided is a composition or biomarker of the present invention for use in therapy or diagnosis, for example in relation to cancer, optionally wherein the cancer is selected from prostate cancer, non-small cell lung cancer and breast cancer.

Another aspect of the present invention relates to an antibody or fragment thereof that binds to a biomarker of the present invention for use in a method of imaging disease, for example cancer in a patient, optionally wherein the cancer is selected from prostate cancer, non-small cell lung cancer and breast cancer.

Preferably, the antibodies or fragments thereof described herein specifically bind to a biomarker of the present invention.

In preferred embodiments, the methods and compositions of the invention are for treatment or diagnosis of disease at an early stage, for example, before symptoms of the disease appear.

In some embodiments, the methods and compositions of the invention are for treatment or diagnosis of disease at a clinical stage According to another aspect of the present invention, there is provided a kit for use in the methods or uses described above, wherein the kit comprises a ligand, for example an antibody or fragment thereof as described herein, capable of binding or specifically recognising the biomarker, detectable in a body fluid and reporter means.

Preferably, the kit is an array or chip.

Preferably, the kit comprises a microtitre plate, test strip, array or chip.

Preferably, the kit comprises instructions for use in accordance with the methods, uses and/or compositions of the present invention.

DETAILED DESCRIPTION OF THE INVENTION

Example embodiments of the present invention will now be described with reference to the accompanying figures.

FIG. 2 shows the nucleic acid sequence of TMEM92 (SEQ ID NO:1);

FIG. 8 shows TMEM92 protein in PC3 cells. Fluorescent microscopy using an anti-TMEM92 antibody (green). (A)

Cells made permeable by exposure to detergent. The nucleus is stained with DAPI (blue). (B) Non-permeable cell to show surface expression of TMEM-92. Scale bar: 5 µm.

The invention relates to methods and compositions for treating disease, for example cancer and to biomarkers, preferably, wherein the cancer is selected from prostate cancer, non-small cell lung cancer and breast cancer.

TMEM92 is a novel cell surface protein that is differentially expressed in cancer as opposed to normal tissue. The data provided herein shows that it could be used as a marker of cancer, for example in tissue sections or when present in certain bodily fluids, and as a target in cancer, for example by using an antibody that recognises it or by blocking its activity through, for example, a small molecule drug.

Within this specification, the term "about" means plus or minus 20%, more preferably plus or minus 10%, even more preferably plus or minus 5%, most preferably plus or minus 2%.

As used herein, the term "therapeutically effective amount" means the amount of a composition which is required to reduce the severity of and/or ameliorate at least one condition or symptom which results from the disease in question.

Within this specification embodiments have been described in a way which enables a clear and concise specification to be written, but it is intended and will be appreciated that embodiments may be variously combined or separated without parting from the invention.

For clinical use, a compound according to the present invention or prodrug form thereof is formulated into a pharmaceutical formulation which is formulated to be compatible with its intended route of administration, for example for oral, rectal, parenteral or other modes of administration. Pharmaceutical formulations are usually prepared by mixing the active substance with a conventional pharmaceutically acceptable diluent or carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. Examples of pharmaceutically acceptable diluents or carrier are water, gelatin, gum arabicum, lactose, microcrystalline cellulose, starch, sodium starch glycolate, calcium hydrogen phosphate, magnesium stearate, talcum, colloidal silicon dioxide, and the like. The use of such media and agents for pharmaceutically active substances is well known in the art. Except insofar as any conventional media or agent is incompatible with the active compound, use thereof in the compositions is contemplated.

Such formulations may also contain other pharmacologically active agents, and conventional additives, such as stabilizers, wetting agents, emulsifiers, flavouring agents, buffers, and the like.

The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum mono stearate and gelatin.

Sterile injectable solutions can be prepared by incorporating the active compound (e.g., a compound according to an embodiment of the invention) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

Preferably, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

Within this specification, "identity," as it is known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. Percentage identity can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988), all of which are incorporated herein by reference in their entirety. Preferred methods to determine identity are designed to give the largest match between the sequences tested. Methods to determine identity are codified in publicly available computer programs. Preferred computer program methods to determine percentage identity between two sequences include, but are not limited to, the GCG program package (Devereux, J., et al., Nucleic Acids Research 12(1): 387 (1984), which is incorporated herein by reference in its entirety), BLASTP, BLASTN, and FASTA (Atschul, S. F. et al., J. Molec. Biol. 215: 403-410 (1990), which is incorporated herein by reference in its entirety). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990), which is incorporated herein by reference in its entirety). As an illustration, by a polynucleotide having a nucleotide sequence having at least, for example, 95% "identity" to a reference nucleotide sequence of "SEQ ID NO: A" it is intended that the nucleotide sequence of the polynucleotide is identical to the reference sequence except that the polynucleotide sequence may include up to five point mutations per each 100 nucleotides of the reference nucleotide sequence of "SEQ ID NO: A." In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of "SEQ ID NO:B" is intended that the amino acid sequence of the polypeptide is identical to the reference sequence except that the polypeptide sequence may include up to five amino acid alterations per each 100 amino acids of the reference amino acid of "SEQ ID NO: B." In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As used herein, the term "hybridizes under stringent conditions" is intended to describe conditions for hybridization and washing under which nucleotide sequences encoding a receptor at least 50% homologous to each other typically remain hybridized to each other. The conditions can be such that sequences at least about 65%, at least about 70%, or at least about 75% or more homologous to each other typically remain hybridized to each other. Such stringent conditions are known to those skilled in the art and can be found in Current Protocols in Molecular Biology, John Wiley & Sons, N.Y. (1989), 6.3.1-6.3.6, which is incorporated herein by reference in its entirety. One example of stringent hybridization conditions are hybridization in 6× sodium chloride/sodium citrate (SSC) at about 45° C., followed by one or more washes in 0.2×SSC, 0.1% SDS at 50-65° C. In one embodiment, an isolated receptor nucleic acid molecule that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

Within this specification, "antibody or antibody fragment" refers to an antibody (for example IgG, IgM, IgA, IgD or IgE) or fragment (such as a Fab, F(ab')2, Fv, disulphide linked Fv, scFv, closed conformation multispecific antibody, disulphide-linked scFv, diabody) whether derived from any species naturally producing an antibody, or created by recombinant DNA technology; whether isolated from serum, B-cells, hybridomas, transfectomas, yeast or bacteria.

Within this specification, the term "treatment" means treatment of an existing disease and/or prophylactic treatment in order to prevent incidence of a disease. As such, the methods of the invention can be used for the treatment, prevention, inhibition of progression or delay in the onset of disease.

The term "biomarker" is used throughout the art and means a distinctive biological or biologically-derived indicator of a process, event or condition. In other words, a biomarker is indicative of a certain biological state, such as the presence of cancerous tissue. In some cases, different forms of biomarkers can be indicative of certain disease states but, without being bound by theory, it is thought that merely the presence of elevated levels of the biomarkers of the present invention in body fluids or tissues is indicative of cancer. Although it is not currently envisaged that different glycoforms, for instance, of the TMEM92 peptide, are secreted, these are nevertheless encompassed by the present invention. For instance, different glycoforms, such as altered glycoform structure or sugar content, may yet be determined for TMEM92, but these are encompassed and may even also be indicative of the progress of cancer. Truncations, mutations, or deletions of, or ligations to, the TMEM92 peptide, or fragment thereof, are also envisaged.

As discussed above, it has surprisingly been found that there is a significant increase in expression of the TMEM92 gene in cancer derived samples compared to normal samples. In many instances, whilst there is expression in cancer derived samples, there is no expression at all in corresponding normal samples. The biomarkers of the present invention can therefore be said to be cancer specific biomarkers.

Figure 6:
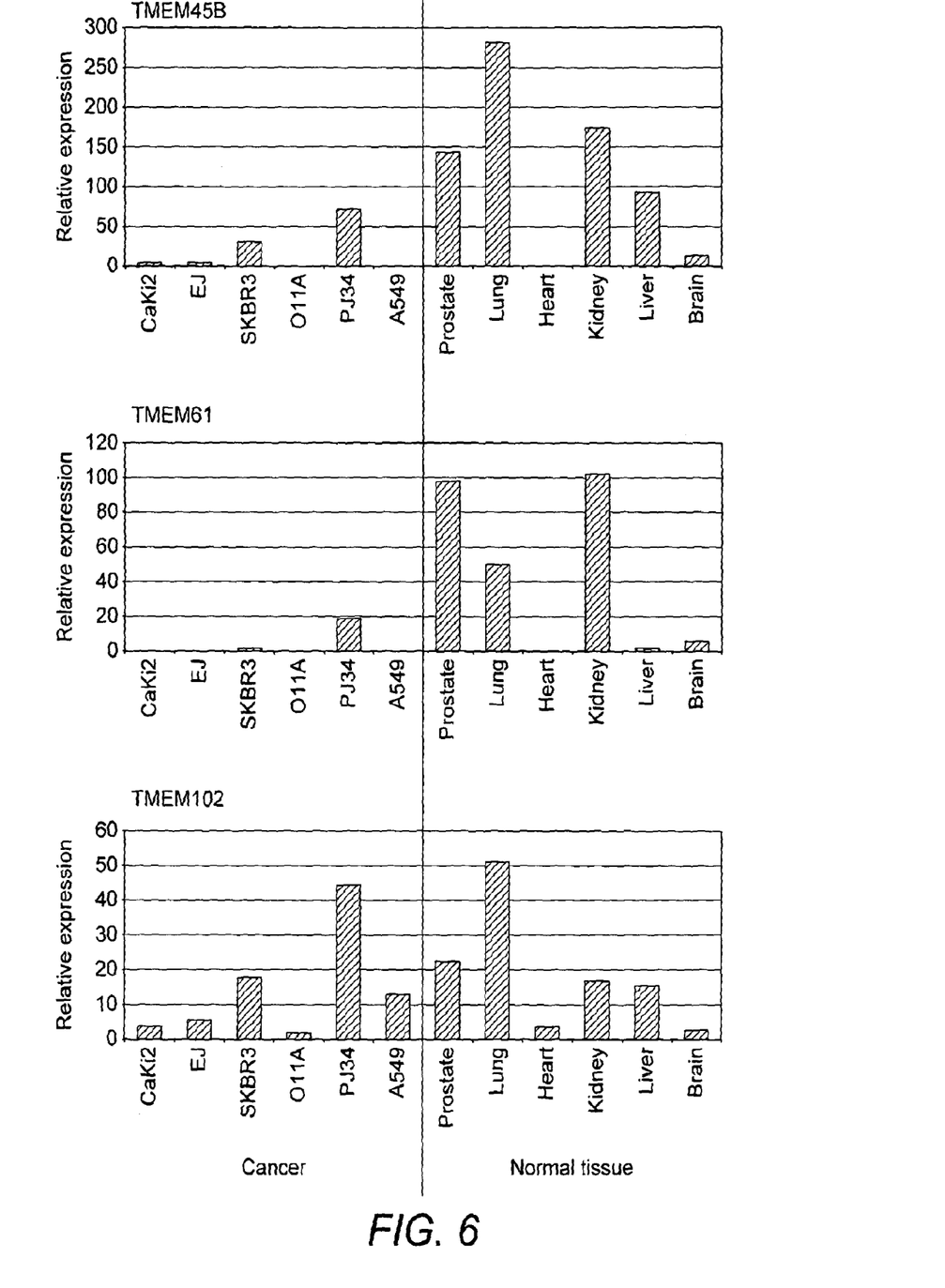
FIG. 6** shows expression data for three other TMEMs.

The results obtained for TMEM92 (FIG. 4) are especially surprising when compared with the results obtained with other TMEM genes (FIG. 6).

It is another advantage of the present invention that an accurate diagnosis can be provided without resorting to unpleasant and potentially harmful invasive procedures, which may also be inaccurate. Furthermore, the present invention is particularly sensitive. Preferably the methods of the present invention may detect the onset of cancer prior to any other detection method and prior to the onset of the overt symptoms of cancer. Thus, the cancer may be treated at an early stage when it is more susceptible to such treatment and less likely to have entered the metastatic stage.

The biomarkers of the present invention can be used in methods of diagnosis, for instance clinical screening, and in methods of prognosis assessment, monitoring the results of therapy, identifying patients most likely to respond to a particular therapeutic treatment, drug screening and development. Furthermore, the biomarkers of the present invention and uses thereof are valuable for identification of new drug treatments and for discovery of new targets for drug treatment.

The term "diagnosis" encompasses identification, confirmation, and or characterisation of the presence or absence of disease, for example cancer, together with the developmental stage thereof, such as early stage or late stage, or benign or metastatic cancer.

EXAMPLES

TMEM92 (NM_153229) is a previously uncharacterised gene predicted to encode a 159 amino acid (17.2 kDa) protein with a single transmembrane domain (FIG. 1). Our data shows that it is not expressed in many normal adult tissues, and is expressed at only a very low level in the liver, colon, lung and uterus (FIG. 4). However, it is strongly expressed in the cancer derived cell lines PC3 (prostate cancer), A549 (non-small cell lung cancer), and MDA-MB-231 (breast cancer).

This differential expression indicates that TMEM92 could be a potential target in cancer. To explore this possibility further, we used a siRNA knock down of TMEM92 in PC3 cells (derived from a metastatic prostate cancer), and WPMY-1 cells (a non-malignant cell line derived from normal prostate fibroblasts). The siRNA used had the following sequence:

```
                                            (SEQ ID NO: 3)
    Forward:    5' GCUUCAGGCCUGAAGAAUA 3',
    and (SEQ ID NO: 4)
    Reverse:    5' UAUUCUUCAGGCCUGAAGC 3'.
```

Figure 5:
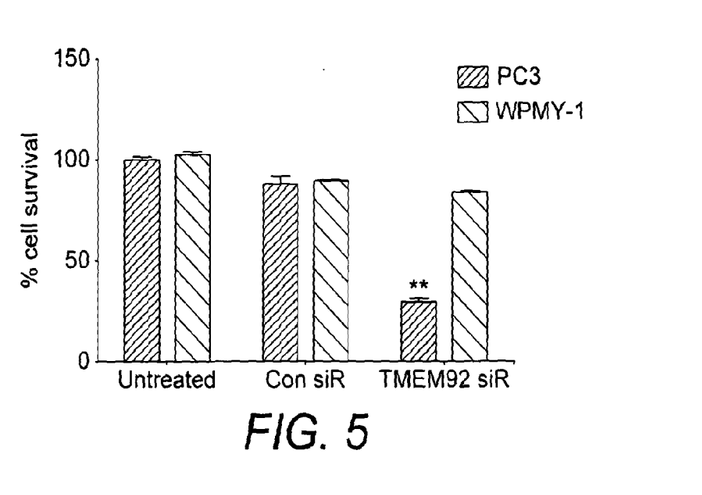
FIG. 5 shows siRNA knock down of TMEM92 in PC3 and WPMY-1 cells. "Con siR"=control (non-specific) siRNA, "TMEM92 siR"=TMEM92 specific siRNA. p<0.01 for cell survival in TMEM92 siRNA treated PC3 v WPMY-1 cells.

Knock down of TMEM92 in PC3 caused a significant reduction in cell survival as compared to a control siRNA (FIG. 5), whilst TMEM92 knock down in WPMY-1 cells does not cause cell death.

These results indicate that TMEM92 could be a useful therapeutic target in cancer, for example through (i) knock down of the TMEM92 gene by siRNA, as described above, (ii) antibody binding to TMEM92 protein to block its function and/or target cells for immune mediated killing, and (iii) a small molecule antagonist of TMEM92 function.

In addition, the differential expression of TMEM92 indicates that it could be useful as a biomarker for cancer.

TMEM92 has not previously been shown to be present on cancer cells. In addition, the ability to kill cancer cells by blocking TMEM92 makes it a very important target.

Despite there being many diagnostic and therapeutic approaches to cancer, none are perfect and many are of limited value. Diagnostic tests often give false positive or negative results, and therapeutics may become ineffective due to innate or developed resistance of cancer cells. The high expression of TMEM92 in cancer together with its role in cancer cell survival (shown by knock down studies to be required for cancer cell survival) indicate that it could make a useful contribution to both diagnostics and targeting.

The results obtained for TMEM92 were repeated for three other TMEMs. The expression data obtained (FIG. 6) for the three other TMEMs shows that these TMEMs are expressed more highly in normal adult tissues than in cancer, this being the exact opposite of the results obtained for TMEM92. Accordingly, this provides further evidence of the surprising nature of the results presented herein for TMEM92.

Figure 7:
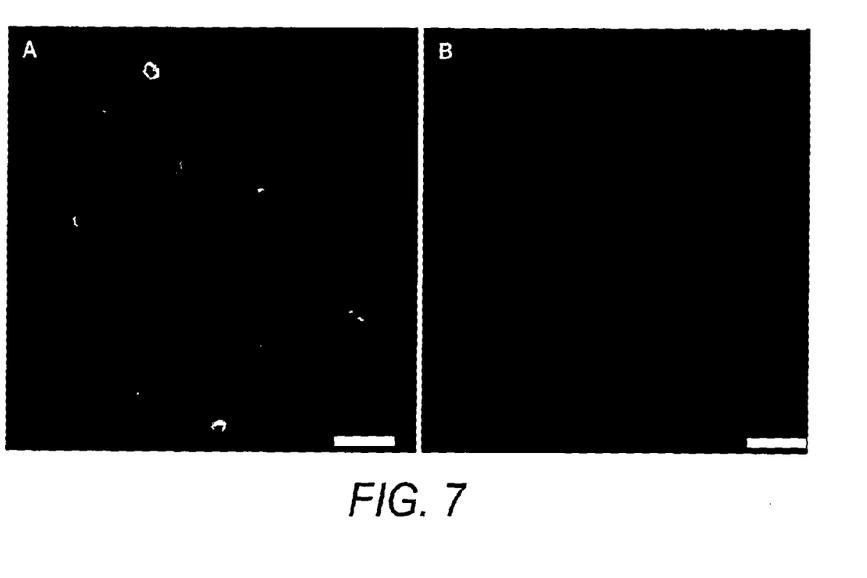
FIG. 7 shows TMEM92 protein is present in PC3 cells but not WMPY-1 cells. Fluorescent microscopy using an anti-TMEM92 antibody (green). (A) PC3 cells (nuclear, cytoplasmic and membrane staining evident), (B) WPMY-1 cells (no staining). The nuclei are stained with DAPI (blue). Scale bar: 50 µm.
Figure 8:
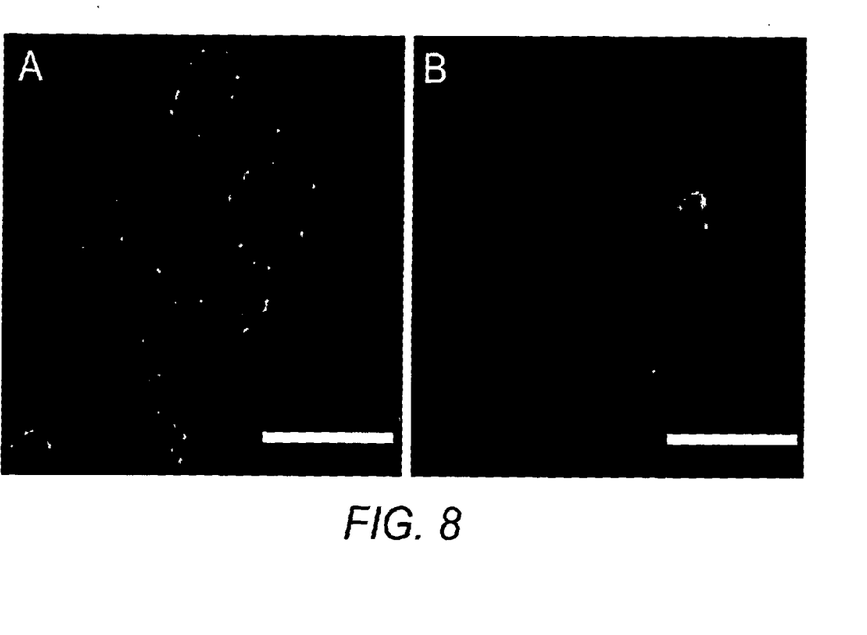

As shown in FIGS. 7 and 8, prostate cancer cells express high levels of TMEM92 protein, in contrast to WPMY-1, a non-malignant cell line derived from normal prostate epithelial cells (FIG. 7). TMEM92 is present in the nucleus, cytoplasm and membrane (FIG. 8), and is secreted by cells into the culture medium. Furthermore, TMEM92 protein can be detected in the urine of men with prostate cancer but is not present in aged matched controls, indicating that it could be used as a biomarker for this disease.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications are covered by the appended claims.

What is claimed is:

1. A method of detecting a TMEM92 biomarker in a patient having prostate cancer, the method comprising:
   a) obtaining a sample of biological fluid or tissue from the patient having prostate cancer; and
   b) detecting whether the TMEM92 biomarker is present in the sample by contacting the sample with an anti-TMEM92 antibody, or fragment thereof, that specifically binds to the TMEM92 biomarker and detecting binding between the TMEM92 biomarker and the antibody;
   wherein the TMEM92 biomarker comprises the amino acid sequence of SEQ ID NO: 2.

2. The method of claim 1, wherein said sample is at least one of urine, semen, blood, cells collected from urine and circulating tumor cells.

3. The method claim 1, wherein the prostate cancer is stage 1 prostate cancer, stage 2 prostate cancer, stage 3 prostate cancer, or stage 4 prostate cancer.

* * * * *

SEQUENCE LISTING

```
<160> NUMBER OF SEQ ID NOS: 4

<210> SEQ ID NO 1
<211> LENGTH: 2747
<212> TYPE: DNA
<213> ORGANISM: Homo sapien

<400> SEQUENCE: 1
ataggtggag agaagtggga gaggtcgcag ccccgccttc tctacacagg aaagctcagt      60
ggcccccaag ccaggatgtc ccaagcttgg gtccccggcc tcgcgcccac cttgctgttc     120
agcctgctgg ctggccccca aaagattgca gccaaatgtg gtctcatcct tgcctgcccc     180
aaaggattca aatgctgtgg tgacagctgc tgccaggaga acgagctctt ccctggcccc     240
gtgaggatct tcgtcatcat cttcctggtc atcctgtccg tcttttgcat ctgtggcctg     300
gctaagtgct tctgtcgcaa ctgcagagag ccggagccag acagcccagt ggattgccgg     360
gggcccctgg aactgccctc catcatcccc cagagaggg tcagagtatc cctttctgcg     420
cccccacccc cctacagtga ggtgattctg aagcccagcc tgggcccaac tcccacagag     480 ccacccctc cctacagctt caggcctgaa gaatataccg gggatcagag gggcattgac     540
aacccggcct tctgagtcac ctcctgcctg gaatcttgcc atcagcaacc tcctccccag     600
tgcctcctgg atcaagctag agactgctgg caccccagga atgtccctgc ccatcctgcc     660
gtgtctctgt tcattcttgg atttaactta ttactttttc tgcttctgtt tccaccccag     720
ctgcctctct tgtcctgagg gttaggctgg agtgacagtt tccgcccacc ccccagccca     780
agaaagaggc tgccggaaag aaaatgctga ccattggagg tgcccaacag tagaatgggc     840
tactgtgagg ggtagtaaga gccccatttc tggaggtatg caaatcttga ctggacagcc     900
agctctgaga ttttatcagg gcacttctat acctgtggga cattggactg gatgagccct     960
```

| | | | |
|---|---|---|---|
| gagccagctt | ccactcctac | ctgaatagag | aactcactgc acccaccac aacacatgat | 1020 |
| aaacacatgt | cctcactgaa | tgttactgat | tgcggctgag ggcctgcctc tggctgtgtg | 1080 |
| gggaggtggg | tggagaggtg | agcccaggca | ctgctgaggg gtgcggtgat ggggtcgctg | 1140 |
| cgccgcaatc | ccaccactga | tgagccacct | gggaggtctg gaggacagt ccatccatgg | 1200 |
| gccgccctcg | gagagaggct | tgttctagat | gtattggctg tctgtttttt gatgtctctg | 1260 |
| tgtgccaaac | agcctggaaa | tggggtacgc | gtgtcccttg tgtgggtttc caatcccttt | 1320 |
| ccgcccaagg | ctttcctggg | acacatggag | cccagctctc tggctgtctt accatgagaa | 1380 |
| gttggtaagt | tggctgtgag | ggggttggat | ccaggaagca gccctgggac agcccattct | 1440 |
| gctgttgata | gcaggaaacc | acctgctggg | agacaatggg ggtggggaaa agcccaggag | 1500 |
| agcagtgggt | ggggctgggc | atccgtggag | tggggcttta ggagaccttg aacgccccca | 1560 |
| ccctggaatc | tcctacagga | aggtgaggag | gtggcaggtt ccacccttct ctaccagccc | 1620 |
| cgctcgctcg | tgggagttaa | cccccctaggg | gagaagagtc ttcactgggg ttcgacccat | 1680 |
| ggggggcctgg | catagtcatg | cagaatgggg | cgggacaatg ccaatgcctt gggactcaga | 1740 |
| cagggctgag | tgcctccacc | ctgattttttg | cctctgcact cgcccccac agcccactca | 1800 |
| atgccagcct | ccttctccag | gcagagagcc | ccatgtcaat gctggccaaa gctctcagga | 1860 |
| ggattggagg | tagaactggc | cctggtatgc | caacaggggt gcctctttta gtgctctccc | 1920 |
| aataatgctc | atcctggggg | catcaggacg | caggcaggtg gcagagctgg gggcagcttg | 1980 |
| atggcacagg | cagccccaaa | gatgccagga | acagggactg tccgggtgtg ggttcccagt | 2040 |
| gagataggc | cctggaagga | gtgcagcagt | tactgacaat atagtgccag ggttggccat | 2100 |
| aggagaatga | gcccaagcgt | aagtggaagt | ttcccttttac tttcagggat tggtcagggg | 2160 |
| tggcagaaaa | catgtgggtt | ctttgtgtag | atgtggctag ttccaattag agaagtcctg | 2220 |
| cagctgatgt | tgccctcacc | gtgatagcag | gaggatgttg agaaatgggc ttggagacc | 2280 |
| tggaggagaa | gttaccctcg | gcccagacgt | tgccttcctt tcatcacagg gcctttaact | 2340 |
| cctcctaggg | agtagcagag | tggccctagg | gaaagtggcc atcctgaaac ctagtgttgc | 2400 |
| tgtgacctgg | tgacagaaat | ggaaacctct | gtggctcttc tggtcatcct tggtgggagt | 2460 |
| gggaatggtg | tcacctttct | agagggccat | ctggcaccat gtaatcacgc cacagatctt | 2520 |
| tacgaagctc | ctgctatgta | ggaaacacta | tgcctggcac tgggtatcca ttaaaatgta | 2580 |
| aaatgcacgt | gacctggcaa | ttccacttct | agaaatgagc cttcagaagt gctcatacaa | 2640 |
| aagagctcaa | taagtatcat | gcactaattc | attgtgccac cagagctccc tatgcagcct | 2700 |
| tttaaaagaa | taaataggat | ctgtagcacc | aaaaaaaaaa aaaaaa | 2747 |

<210> SEQ ID NO 2
<211> LENGTH: 159
<212> TYPE: PRT
<213> ORGANISM: Homo sapiens

<400> SEQUENCE: 2

Met Ser Gln Ala Trp Val Pro Gly Leu Ala Pro Thr Leu Leu Phe Ser
 1               5                  10                  15

Leu Leu Ala Gly Pro Gln Lys Ile Ala Ala Lys Cys Gly Leu Ile Leu
             20                  25                  30

Ala Cys Pro Lys Gly Phe Lys Cys Cys Gly Asp Ser Cys Cys Gln Glu
         35                  40                  45

Asn Glu Leu Phe Pro Gly Pro Val Arg Ile Phe Val Ile Ile Phe Leu

```
                50                  55                  60
Val Ile Leu Ser Val Phe Cys Ile Cys Gly Leu Ala Lys Cys Phe Cys
 65                  70                  75                  80

Arg Asn Cys Arg Glu Pro Glu Pro Asp Thr Pro Val Asp Cys Arg Gly
                 85                  90                  95

Pro Leu Glu Leu Pro Ser Ile Ile Pro Pro Glu Arg Val Arg Val Ser
                100                 105                 110

Leu Ser Ala Pro Pro Pro Tyr Ser Glu Val Ile Leu Lys Pro Ser
                115                 120                 125

Leu Gly Pro Thr Pro Thr Glu Pro Pro Pro Tyr Ser Phe Arg Pro
                130                 135                 140

Glu Glu Tyr Thr Gly Asp Gln Arg Gly Ile Asp Asn Pro Ala Phe
145                 150                 155

<210> SEQ ID NO 3
<211> LENGTH: 19
<212> TYPE: RNA
<213> ORGANISM: unknown
<220> FEATURE:
<223> OTHER INFORMATION: Forward  siRNA of TMEM92

<400> SEQUENCE: 3
gcuucaggcc ugaagaaua                                                    19

<210> SEQ ID NO 4
<211> LENGTH: 19
<212> TYPE: RNA
<213> ORGANISM: Unknown
<220> FEATURE:
<223> OTHER INFORMATION: Reverse siRNA of TMEM92

<400> SEQUENCE: 4
uauucuucag gccugaagc                                                    19
```